US00PP16234P2

(12) United States Plant Patent
Lemon

(10) Patent No.: US PP16,234 P2
(45) Date of Patent: Feb. 7, 2006

(54) ***GERANIUM* PLANT NAMED 'MAESTRO RICH RED'**

(50) Latin Name: *Pelargonium×hortorum*
Varietal Denomination: Maestro Rich Red

(75) Inventor: David G. Lemon, Lompoc, CA (US)

(73) Assignee: Oglevee, Ltd., Connellsville, PA (US)

( * ) Notice: Subject to any disclaimer, the term of this patent is extended or adjusted under 35 U.S.C. 154(b) by 89 days.

(21) Appl. No.: 10/946,382

(22) Filed: Sep. 21, 2004

(51) Int. Cl.
*A01H 5/00* (2006.01)

(52) U.S. Cl. ..... Plt./330

(58) Field of Classification Search ..... Plt./330
See application file for complete search history.

*Primary Examiner*—Kent Bell
(74) *Attorney, Agent, or Firm*—The Webb Law Firm

(57) ABSTRACT

'Maestro Rich Red' is a new variety of *Geranium* having early flowering, good leaf zoning, excellent outdoor performance, and distinct cranberry red flowers.

1 Drawing Sheet

Botanical classification: *Pelargonium×hortorum.*
Varietal denomination: 'Maestro Rich Red'.

BACKGROUND OF THE INVENTION

The present invention comprises a new and distinct cultivar of *Pelargonium×hortorum* known by the varietal name 'Maestro Rich Red', Breeder No. 6DG2808. The new variety was discovered in Lompoc, Calif. The new variety is a result of cross breeding Seedling 1269 (female parent) (unpatented) and 'Sassy Dark Red' (male parent) (U.S. Plant Pat. No. 8,053). The new variety exhibits similar flower color to both parents, but blooms earlier and has better outdoor performance than both parents. The new variety was first asexually reproduced by cuttings in Connellsville, Pa. The new variety has been trial and field tested and has been found to retain its distinctive characteristics and remain true to type through successive asexual propagations.

The new variety was grown in a glass greenhouse in Connellsville, Pa. using full light, 60° F. night temperature and 68° F. day temperature and grown in a soilless media with constant fertilizer at 200–250 ppm nitrogen and potassium. The new variety exhibits rooting at 14 days under optimal conditions and has a response time of seven weeks from a rooted cutting to flowering.

DESCRIPTION OF THE DRAWING

The accompanying photographic drawing illustrates the new variety, with the color being as nearly true as is possible with color illustrations of this type.

DESCRIPTION OF THE PLANT

Figure 1:
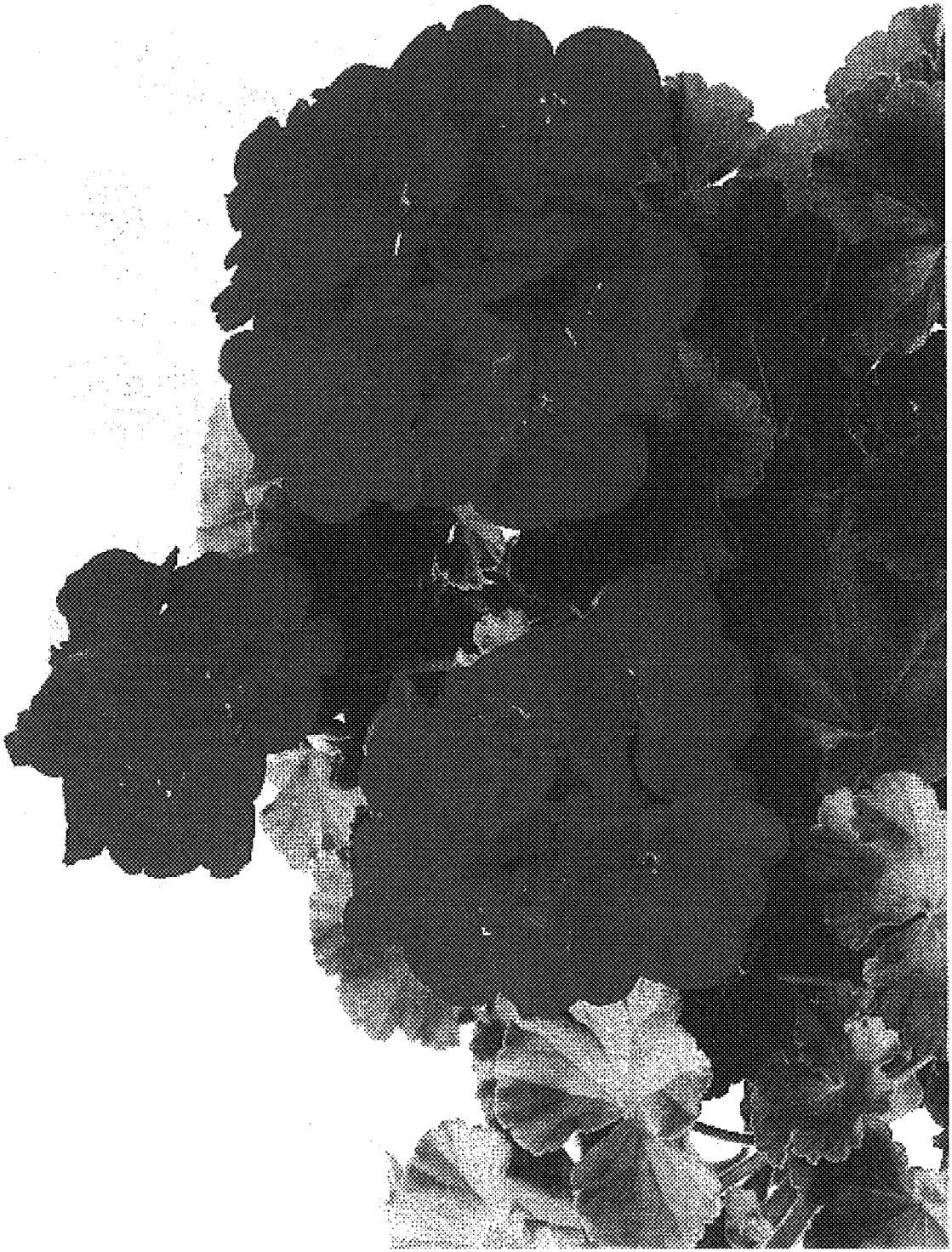

The following detailed description sets forth the characteristics of the new cultivar. The data which defines these characteristics were collected by asexual reproductions carried out in Connellsville, Pa. Plants described were 9 weeks old. The color readings were taken indoors under 65–85 foot candles of cool white fluorescent light. Color references are primarily to The R.H.S. Colour Chart of The Royal Horticultural Society of London.

PLANT

Form: Medium mound.
Growth: Upright mound, with free basal branching.
Height from media surface: 13–16 cm in a 4 inch pot from the top of the soil to the top of the plant.
Strength: Does not require artificial support.
Rooting time: From a rooted cutting, the response time was seven weeks to flowering.
Foliage: Stalked leaf attachment of a medium green color with zonation present.
Leaves:
- *Arrangement.*—Alternate.
- *Size.*—5.2–6.3 cm long at longest point; 6.5–7.3 cm across at widest point.
- *Zone.*—Present 1.5–1.7 cm from point of attachment; the zone is 1.1–1.5 cm wide.
- *Shape.*—Reniform, with a cordate base.
- *Margin.*—Crenate.
- *Texture.*—Velvety.
- *Pubescence.*—Present.
- *Color.*—Upper surface: 137B. Lower surface: 138A. Zone: 139A.
- *Ribs and veins.*—Type: Palmate. Color: 146C.
- *Stipules.*—Two per node.

Petioles:
- *Color.*—144A, with accent pigmentation of 183A.
- *Length.*—5.8–6.1 cm.

Stem:
- *Color.*—144A.
- *Internode length.*—1.5–2.3 cm.

THE BUD (Characteristics measured just before anthesis)

*Shape.*—Cluster: Elliptical when no color is showing, having 30–42 buds per cluster. Individual bud: Elliptical or oval when no color is showing.
*Size.*—Cluster: 3.5–4.2 cm across. Individual bud: 0.8 cm long, 0.6 cm wide.

INFLORESCENCE

Blooming habit: Continuous; free and early blooming.

Umbel size: 9.0–11.0 cm across.

Borne: Umbel; flowers on pedicel; pedicel on peduncle; 5.0–8.0 cm above foliage.

Number of flowers per umbel: 38.

Flowers:

*Form.*—Slightly cupped; petals overlap and petaloids give a ruffled appearance.

*Size.*—4.8–5.0 cm across; 1.0–1.7 cm deep.

*Petals.*—Shape: Inverted teardrop. Size: 2.8–3.2 cm long; 1.9–2.6 cm across. Margin: Entire. Number per flower: 5–9. Texture: Smooth; velvety; highly reflective. Tonality from a distance: Bright cherry red flowers with accents of bright orange at the middle of the flower atop a mound of medium green foliage. Color: Upper petals (ranging between 3–4 in number) have an area of electric watermelon orange-red, while the lower petals lack these bright highlights. Upper surface: Upper petals: 45B at outer edge moving to 46B and then to 57A and further to 43C and 47C near the white, about 155A, base of the petal. Darker veining of 46A is present. Lower petals: 46B at outer edge moving to 57A and white, about 155A, at the very base. Darker veining of 46A is present. Lower surface: Upper petals: 46B at outer edge moving to areas of 46C and 45C and 46D toward the white, about 155A, petal base. Darker veining of 46A shows through from the front. Lower petals: 46C at outer edge moving to 47B and then to 47C toward the white, about 155A, petal base. Veining of 54A shows through.

Petaloids:

*Number.*—2–6.

*Shape.*—Irregular; some are twisted; tubular; petal-shaped with cut margin; anther-like holding pollen.

*Color.*—Same as petals.

Pedicel:

*Length.*—3.1 cm.

*Color.*—144B at the very base. The majority of each pedicel is 187C.

Peduncle:

*Length.*—10.5–13.5 cm.

*Color.*—144A, with light staining of 187C.

Disease/pest resistance: No susceptibility to diseases or pests has been noted to date.

Lasting quality: Overall blooming habit is continuous throughout the flowering season. Individual umbels last 7–14 days depending on weather conditions.

REPRODUCTIVE ORGANS

Stamens:

*Anthers.*—2.0–3.0 mm long.

*Filaments.*—Length: 8.0–10.0 mm. Color: White at base, pink with watermelon pink tips.

*Pollen color.*—Golden orange.

Pistils:

*Number.*—One.

*Length.*—1.0–1.1 cm.

*Stigma.*—Number: One. Color: Burgundy.

*Style.*—Length: 3.0–4.0 mm. Color: Burgundy.

Ovaries:

*Completeness.*—Superior. Length: 7.0–8.0 mm. Width: 3.0–4.0 cm. Color: Green. Pubescence: Present.

Fruit: None observed.

I claim:

1. A new and distinct variety of *Geranium* plant named 'Maestro Rich Red' as described and illustrated.

* * * * *